(12) United States Patent
Mead et al.

(10) Patent No.: US 11,986,678 B2
(45) Date of Patent: *May 21, 2024

(54) METHOD OF CALIBRATING A PATIENT MONITORING SYSTEM FOR USE WITH A RADIOTHERAPY TREATMENT APPARATUS

(71) Applicant: VISION RT LIMITED, London (GB)

(72) Inventors: Edward William Mead, London (GB); Ivan Daniel Meir, London (GB)

(73) Assignee: VISION RT LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/107,879

(22) Filed: Feb. 9, 2023

(65) Prior Publication Data

US 2023/0181933 A1  Jun. 15, 2023

Related U.S. Application Data

(63) Continuation of application No. 17/549,618, filed on Dec. 13, 2021, now Pat. No. 11,612,766, which is a (Continued)

(30) Foreign Application Priority Data

Aug. 2, 2017 (GB) ..................................... 1712462

(51) Int. Cl.
*A61N 5/10* (2006.01)

(52) U.S. Cl.
CPC .... *A61N 5/1075* (2013.01); *A61N 2005/1076* (2013.01)

(58) Field of Classification Search
CPC ...................... A61N 5/1075; A61N 2005/1076
See application file for complete search history.

(56) References Cited

U.S. PATENT DOCUMENTS

| 4,296,329 A | 10/1981 | Mirabella |
| 2002/0080909 A1 | 6/2002 | Op De Beek |

(Continued)

FOREIGN PATENT DOCUMENTS

WO   WO 2014/022480 A1   2/2014

OTHER PUBLICATIONS

Grimm et al., "A quality assurance method with submillimeter accuracy for stereotactic linear accelerators," Journal of Applied Clinical Medical Physics, vol. 12, No. 1, 2011, pp. 182-198.

(Continued)

*Primary Examiner* — Blake C Riddick
(74) *Attorney, Agent, or Firm* — Birch, Stewart, Kolasch & Birch, LLP

(57) ABSTRACT

A method of calibrating a monitoring system (10,14) is described in which a calibration phantom (70) is located with its center located approximately at the isocenter of a treatment room through which a treatment apparatus (16) is arranged to direct radiation, wherein the surface of the calibration phantom (70) closest to an image capture device (72) of the monitoring system (10,14) is inclined approximately 45° relative to the camera plane of an image capture device of the monitoring system. Images of the calibration phantom (70) are then captured using the image capture device (72) and the images are processed to generate a model of the imaged surface of the calibration phantom. The generated model of the imaged surface of the calibration phantom (70) is then utilized to identify the relative location of the center of the calibration phantom (70) and the camera plane of the image capture device (72) which is then utilized to determine the relative location of the camera plane of the image capture device and the isocenter of a treatment room.

19 Claims, 10 Drawing Sheets

Related U.S. Application Data continuation of application No. 16/635,884, filed as application No. PCT/GB2018/052192 on Jul. 31, 2018, now Pat. No. 11,224,765.

(56) References Cited

U.S. PATENT DOCUMENTS

| | | |
|---|---|---|
| 2002/0085668 A1 | 7/2002 | Blumhofer |
| 2004/0022363 A1 | 2/2004 | Ghelmansarai |
| 2004/0228451 A1 | 11/2004 | Wu |
| 2005/0013406 A1 | 1/2005 | Dyk |
| 2006/0002519 A1 | 1/2006 | Jenkins |
| 2006/0036170 A1 | 2/2006 | Lachaine |
| 2009/0022383 A1 | 1/2009 | Falco |
| 2009/0238338 A1 | 9/2009 | Long |
| 2009/0285357 A1 | 11/2009 | Khamene |
| 2011/0085645 A1 | 4/2011 | Paidi et al. |
| 2012/0312961 A1 | 12/2012 | Raleigh |
| 2013/0229495 A1 | 9/2013 | Bani-Hashemi |
| 2014/0016759 A1 | 1/2014 | Ngar et al. |
| 2014/0044141 A1 | 2/2014 | Bouliniere |
| 2015/0085072 A1 | 3/2015 | Yan et al. |
| 2015/0085993 A1* | 3/2015 | Scheib ............. A61N 5/1071 378/207 |
| 2015/0306427 A1 | 10/2015 | Hirasawa |
| 2015/0343239 A1 | 12/2015 | Liu |
| 2015/0352376 A1 | 12/2015 | Wiggers |
| 2016/0023019 A1 | 1/2016 | Filiberti |
| 2016/0129283 A1* | 5/2016 | Meir ............. G06T 7/0012 348/46 |

OTHER PUBLICATIONS

Low et al., "Minimization of target positioning error in accelerator-based radiosurgery," Medical Physics, vol. 22, No. 4, Apr. 1995, pp. 443-448.

Lutz et al., "A system for stereotactic radiosurgery with a linear accelerator", International Journal of Radiation Oncology Biology Physics, vol. 14, No. 2, Feb. 1988, pp. 373-381.

Schreibmann et al., "Automated Quality Assurance for Image-Guided Radiation Therapy", Journal of Applied Clinical Medical Physics, vol. 10, No. 1, 2009, pp. 71-79.

* cited by examiner

METHOD OF CALIBRATING A PATIENT MONITORING SYSTEM FOR USE WITH A RADIOTHERAPY TREATMENT APPARATUS

This application is a Continuation of co-pending application Ser. No. 17/549,618, filed on Dec. 13, 2021, which is a Continuation of co-pending application Ser. No. 16/635,884, filed on Jan. 31, 2020, issued as U.S. Pat. No. 11,224,765 on Jan. 18, 2022, which is a National Phase of PCT International Application No. PCT/GB2018/052192 filed on Jul. 31, 2018, which claims priority under 35 U.S.C. § 119(a) to UK Patent Application No. GB 1712462.9 filed on Aug. 2, 2017. Each of the above applications is hereby expressly incorporated by reference, in its entirety, into the present application.

The present invention concerns a method of calibrating a patient monitoring system for monitoring the location of a patient during radiotherapy. In particular, the present invention concerns a method of identifying the locations of image detectors such as cameras in a monitoring system relative to a treatment room isocenter.

Radiotherapy consists of projecting onto a predetermined region of a patient's body, a radiation beam so as to destroy or eliminate tumors existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful. For this reason, a number of monitoring systems for assisting the positioning of patients during radiotherapy have been proposed such as those described in Vision RT's earlier patents and patent applications in U.S. Pat. Nos. 7,889,906, 7,348,974, 8,135,201, 9,028,422, and US Pat Application Nos. 2015/265852 and 2016/129283, all of which are hereby incorporated by reference.

In the systems described in Vision RT's patents and patent applications, images of a patient are obtained and processed to generate data identifying 3D positions of a large number of points corresponding to points on the surface of a patient. Such data can be compared with data generated on a previous occasion and used to position a patient in a consistent manner or provide a warning when a patient moves out of position. Typically such a comparison involves undertaking Procrustes analysis to determine a transformation which minimizes the differences in position between points on the surface of a patient identified by data generated based on live images and points on the surface of a patient identified by data generated on a previous occasion.

Vision RT's patient monitoring systems are able to generate highly accurate (e.g. sub millimeter) models of the surface of a patient. To do so, the monitoring system is calibrated in order to establish camera parameters identifying the relative locations and orientations of the image capture devices/cameras, any optical distortion caused by the optical design of the lens of each image detector/camera e.g. barrel, pincushion, and moustache distortion and de-centering/tangential distortion, and other internal parameters of the cameras/image capture devices (e.g. focal length, image center, aspect ratio skew, pixel spacing etc.). Once known, camera parameters can be utilized to manipulate obtained images to obtain images free of distortion. 3D position measurements can then be determined by processing images obtained from different locations and deriving 3D positions from the images and the relative locations and orientations of the image capture devices/cameras.

In addition, the monitoring system must also be calibrated so as to identify the relative location of the cameras of the monitoring system and the treatment room isocenter towards which radiation generated by a treatment apparatus is directed.

Originally, the primary method for isocenter verification in radiotherapy was to measure the distance between the tip of a mechanical pointer mounted on the gantry head of a treatment apparatus and a fixed point mounted on the treatment table. Such a method was manual, laborious and time-consuming. The accuracy of the method depended upon the human observer and was also limited by size of the tip of the pointer used.

An improved technique was introduced by Lutz, Winston and Maleki at Harvard Medical School in 1988 which is described in Lutz W, Winston K R, Maleki N. A system for stereotactic radiosurgery with a linear accelerator. Int J Radiat Oncol Biol Phys. 1988; 14(2):373-81. In the Winston-Lutz system, a calibration phantom comprising a small metallic ball made of steel, titanium or tungsten is fixed on the treatment table by a locking mechanism. The phantom position is adjustable in three directions by means of a micrometer tool. The collimator used for radiotherapy is attached to the gantry head and the ball is placed as closely as possible to the isocenter by aligning the marks on the phantom with the treatment room lasers. The collimated beam is used to expose a radiographic test film mounted perpendicular to the beam direction on a stand behind the ball. Differences between the center of the sphere shadow and the field center identifies the differences between the true isocenter and the isocenter as indicated by the treatment room lasers. The offset is read on each film using transparent template guidance scales or by scanning the film and software analysis.

A mathematical method for analyzing radiographic Winston Lutz images was developed and is described in Low D A, Li Z, Drzymala R E. Minimization of target positioning error in accelerator-based radiosurgery. Med Phys. 1995; 22(4):443-48 which used the film-measured isocenter positional errors for eight gantry angle and couch settings to find the suitable offset for the phantom stand to minimize the distance between the treatment apparatus isocenter and the target. A similar aim was followed by Grimm et al., who developed an algorithm to reconstruct the Winston-Lutz phantom ball locus in three dimensions from two-dimensional radiographic film images taken at certain couch and gantry angles and combined them with the images of lasers taken by digital cameras. This approach is described in Grimm J, Grimm S L, Das I J, et al. A quality assurance method with sub-millimeter accuracy for stereotactic linear accelerators. J Appl Clin Med Phys. 2011; 12(1):182-98.

A further example of automated processing of radiographic phantom images is described in E Schriebmann, E Elder and T Fox, Automated Quality Assurance for Image-Guided Radiation Therapy, J Appl Clin Med Phys. 2009:10 (1):71-79 which discusses the automation of Quality Assurance methods to ensure that a megavoltage (MV) treatment beam coincides with an integrated kilo voltage (kV) or volumetric cone beam CT. In the paper, a calibration cube is described as being located at the estimated location of treatment room isocenter using laser markings. Radiographic images of the irradiation of the cube are then obtained and processed to determine the extent the cube as positioned is offset from the isocenter as identified by the MV, kV and volumetric cone beams.

The position of the calibration phantom can then be adjusted based on the analysis of the radiographic Winston Lutz images until the phantom is accurately located at the treatment room isocenter. Having identified the location of the isocenter, the location of the isocenter can then be highlighted by using a set of lasers generating planes of laser lights and to that end many calibration phantoms have exterior markings so that once the phantom has been located at the isocenter, laser lights can be adjusted so that generated planes of laser light coincide with the exterior markings and when the phantom is removed, the location of the isocenter is identified by the intersection of the laser beams.

The positioning of the cameras relative to the isocenter of the treatment apparatus can then be determined by imaging a calibration cube of known size which is positioned on a treatment apparatus at a position with its center at the isocenter of the treatment apparatus. Typically positioning the calibration cube is achieved through the co-incidence of marks on the exterior of the cube with the projection of the laser cross hairs which intersect at the isocenter. Images of the calibration cube are then obtained and processed utilizing the previously obtained measurements of the relative locations of the cameras and any data about the existence of any distortion present in the images and a 3D computer model of the surface of the cube is generated. A comparison between the generated 3D model and the known parameters for the size and position of the calibration cube enables measurements made in the co-ordinate system of the modelling software to be converted into real world measurements in the treatment room relative to the treatment isocenter.

Although the conventional approach to calibrating a stereoscopic camera system for use with a radio therapy treatment apparatus is highly accurate, further improvements in accuracy are desirable.

In accordance with one aspect of the present invention a method of calibrating a monitoring system is provided characterized by a calibration phantom being located with its center located approximately at the isocenter of a treatment room wherein in plan-view the surface of the calibration phantom closest to an image capture device of the monitoring system is inclined approximately 45° relative to the camera plane of an image capture device of the monitoring system. Images of the calibration phantom are then captured using the image capture device and the images are processed to generate a model of the imaged surface of the calibration phantom. The generated model of the imaged surface of the calibration phantom is then utilized to identify the relative location of the center of the calibration phantom and the camera plane of the image capture device which in turn is utilized to determine the relative location of the camera plane of the image capture device and the isocenter of a treatment room through which a treatment apparatus is arranged to direct radiation.

The applicants have determined that angling the surface of a calibration phantom, in particular a calibration cube, so that in plan-view the surface of the calibration phantom closest to an image capture device is inclined approximately 45° relative to the camera plane of an image capture device of a monitoring system improves the accuracy with which such a monitoring system can generate a model of the calibration phantom and hence improves the accuracy with which the relative locations of image capture devices and a treatment room isocenter may be determined.

In some embodiments, locating a calibration phantom with its center located approximately at the isocenter of a treatment room, wherein in plan-view the surface of the calibration phantom closest to an image capture device is inclined approximately 45° relative to the camera plane of the image capture device may comprise using a laser lighting system to highlight the isocenter of a treatment room and positioning the a calibration phantom by aligning laser light used to highlight the isocenter of a treatment room with markings provided on the exterior of the calibration phantom. The markings on a calibration phantom in the form of a calibration cube may comprise markings extending along the edges of the cube; markings bisecting the cube; and/or a cross extending between diagonally opposite corners of the cube.

In some embodiments the calibration phantom may comprise a calibration phantom containing an irradiation target. In such embodiments locating the relative positions of an image capture device of a monitoring system for monitoring the positioning of a patient during radiation treatment and an isocenter of a treatment room through which a treatment apparatus is arranged to direct radiation may comprise obtaining a radiographic image of the calibration phantom irradiated by the treatment apparatus and analyzing the obtained radiographic image to determine the relative location of the treatment room isocenter and the center of the calibration phantom.

In such embodiments the calibration phantom may be repositioned after the relative location of the treatment room of isocenter and the center of the calibration phantom has been identified and images of the repositioned phantom may be obtained by the monitoring system and utilized to determine the relative location of an image capture device and an isocenter of a treatment room.

Alternatively, the relative location of the treatment room of isocenter and the center of the calibration phantom may be used together with a generated model of the calibration phantom without relocating the phantom to determine the relative location of an image capture device and an isocenter of a treatment room.

In some embodiments the monitoring system may comprise a plurality of image capture devices.

In some embodiments the monitoring system may comprise a projector operable to project light onto the surface of an object located in the vicinity of a treatment room isocenter. Such a projector may comprise a projector operable to project structured light in the form of a grid pattern or a line of laser light onto the surface of an object located in the vicinity of the treatment room isocenter. In such a system obtained images of the calibration phantom onto which structured light has been projected may be processed to analyze the distortion of a projected pattern of structured light appearing in the images in order to generate a model of the imaged surface of the calibration phantom.

In other embodiments the projector may comprise a projector operable to project a speckled pattern of light onto the surface of an object located in the vicinity of the treatment room isocenter. In such a system, the monitoring system may comprise a stereoscopic camera system and processing an obtained image to generate a model of the imaged surface of the calibration phantom may comprise processing obtained stereoscopic images of the calibration phantom onto which a speckled pattern of light has been projected and generating a model of the imaged surface of the calibration phantom to identify corresponding portions of the object in the obtained images.

The monitoring system may comprise one or more camera pods each containing one or more image capture devices wherein the camera pods are suspended from the ceiling of the treatment room. Where the monitoring system comprises a plurality of camera pods, the camera pods may all be located on the same side of a treatment room and the camera pods may be arranged in a symmetrical pattern within the treatment room.

In such embodiments a calibration phantom may be arranged with the its center located approximately at the isocenter of a treatment room, where in plan-view the surface of the calibration phantom closest to an image capture device of one of the camera pods is inclined approximately 45° relative to the camera plane of the image capture device on that camera pod.

In some such embodiments the monitoring system may comprise a central camera pod flanked by two other camera pods and locating the calibration phantom may comprise locating a calibration phantom approximately at a treatment room isocenter with the surface of the calibration phantom closest to an image capture device of the centrally located camera pod in plan-view inclined approximately 45° relative to the camera plane of the image capture device on the centrally located camera pod.

In a further aspect of the present invention there is provided a calibration phantom for use in any of the above described methods. Such a calibration phantom may comprise a calibration cube bearing markings on its exterior facilitating the orientation of the cube for imaging by the camera(s)/image capture device(s) of a monitoring system. Such markings may comprise markings selected from markings extending along the edges of the cube; markings bisecting the cube; and a cross extending between diagonally opposite corners of the cube. In some embodiments the calibration phantom may contain an irradiation target operable to be irradiated by a treatment apparatus.

BRIEF DESCRIPTION OF THE DRAWINGS

An embodiment of the present invention will now be described in greater detail with reference to the accompanying drawings in which.

SPECIFIC EMBODIMENTS

Prior to describing a method of determining the relative location of cameras/image detectors of a monitoring system for monitoring the positioning of a patient and an isocenter of a treatment room in accordance with the present invention, a patient monitoring system and radiotherapy treatment apparatus which can be calibrated using the described method and a conventional approach to identifying the relative locations of cameras/image detectors of such a system and the isocenter of a treatment room will first be described with reference to FIGS. 1-5.

Figure 1:
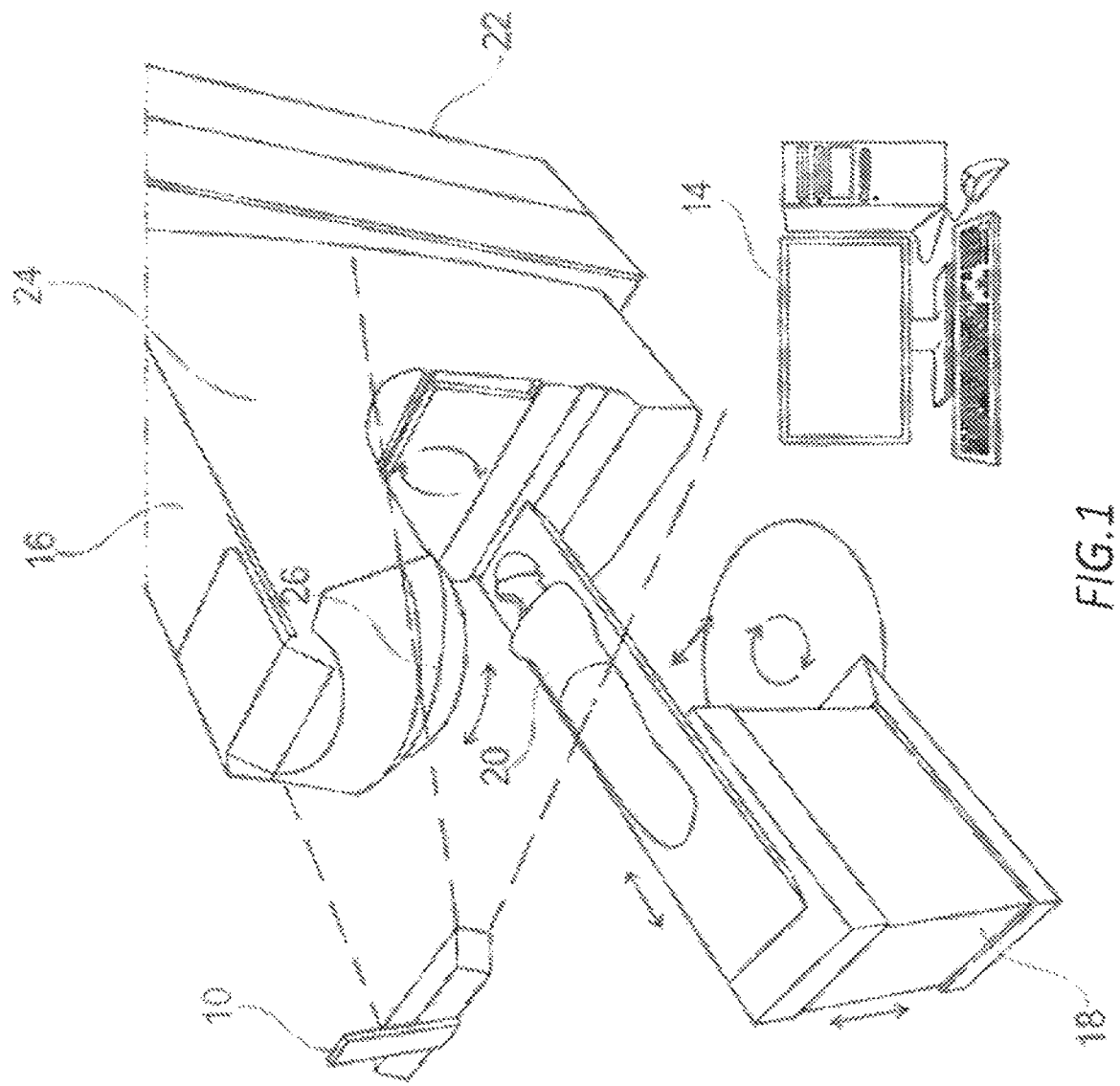
FIG. 1 is a schematic perspective view of a treatment apparatus and a patient monitor.

FIG. 1 is a schematic perspective view of an exemplary patient monitoring system comprising a camera system comprising a number of cameras mounted within a number of camera pods 10 one of which is shown in FIG. 1 that are connected by wiring (not shown) to a computer 14. The computer 14 is also connected to treatment apparatus 16 such as a linear accelerator for applying radiotherapy. A mechanical couch 18 is provided as part of the treatment apparatus upon which a patient 20 lies during treatment. The treatment apparatus 16 and the mechanical couch 18 are arranged such that, under the control of the computer 14, the relative positions of the mechanical couch 18 and the treatment apparatus 16 may be varied, laterally, vertically, longitudinally and rotationally as is indicated in the figure by the arrows adjacent the couch.

The treatment apparatus 16 comprises a main body 22 from which extends a gantry 24. A collimator 26 is provided at the end of the gantry 24 remote from the main body 22 of the treatment apparatus 16. To vary the angles at which radiation irradiates a patient 20, the gantry 24, under the control of the computer 14, is arranged to rotate about an axis passing through the center of the main body 22 of the treatment apparatus 16 as indicated on the figure. Additionally the direction of irradiation by the treatment apparatus may also be varied by rotating the collimator 26 at the end of the gantry 24 as also indicated by the arrows on the figure.

To obtain a reasonable field of view in a patient monitoring system, cameras pods 10 containing cameras monitoring a patient 20, typically view a patient 20 from a distance (e.g. 1 to 2 meters from the patient being monitored). In the exemplary illustration of FIG. 1, the field of view of the camera pod 10 shown in FIG. 1 is indicated by the dashed lines extending away from the camera pod 10.

As is shown in FIG. 1, typically such camera pods 10 are suspended from the ceiling of a treatment room and are located away from the gantry 24 so that the camera pods 10 do not interfere with the rotation of the gantry 24. In some systems a camera system including only a single camera pod 10 is utilized. However, in other systems, it is preferable for the camera system to include multiple camera pods 10 as rotation of the gantry 24 may block the view of a patient 20 in whole or in part when the gantry 24 or the mechanical couch 18 are in particular orientations. The provision of multiple camera pods 10 also facilitates imaging a patient from multiple directions which may increase the accuracy of the system.

A laser lighting system (not shown), typically in the form of a set of laser lights arranged to generate three planes of laser light may be provided to highlight the treatment room isocenter, being the position in the treatment room, through which the treatment apparatus 16 is arranged to direct radiation regardless of the orientation and position of the collimator 26 and gantry 24. When a patient 20 is positioned for treatment, this treatment room isocenter should coincide with the tissue intended to receive the greatest amount of radiation, FIG. 2 is a front perspective view of an exemplary camera pod 10.

The camera pod 10 in this example comprises a housing 41 which is connected to a bracket 42 via a hinge 44. The bracket 42 enables the camera pod 10 to be attached in a fixed location to the ceiling of a treatment room whilst the hinge 44 permits the orientation of the camera pod 10 to be orientated relative to the bracket 42 so that the camera pod 10 can be arranged to view a patient 20 on a mechanical couch 18. A pair of lenses 46 are mounted at either end of the front surface 48 of the housing 41. These lenses 46 are positioned in front of image capture devices/cameras such as CMOS active pixel sensors or charge coupled devices (not shown) contained within the housing 41. The cameras/image detectors are arranged behind the lenses 46 so as to capture images of a patient 20 via the lenses 46.

Figure 2:
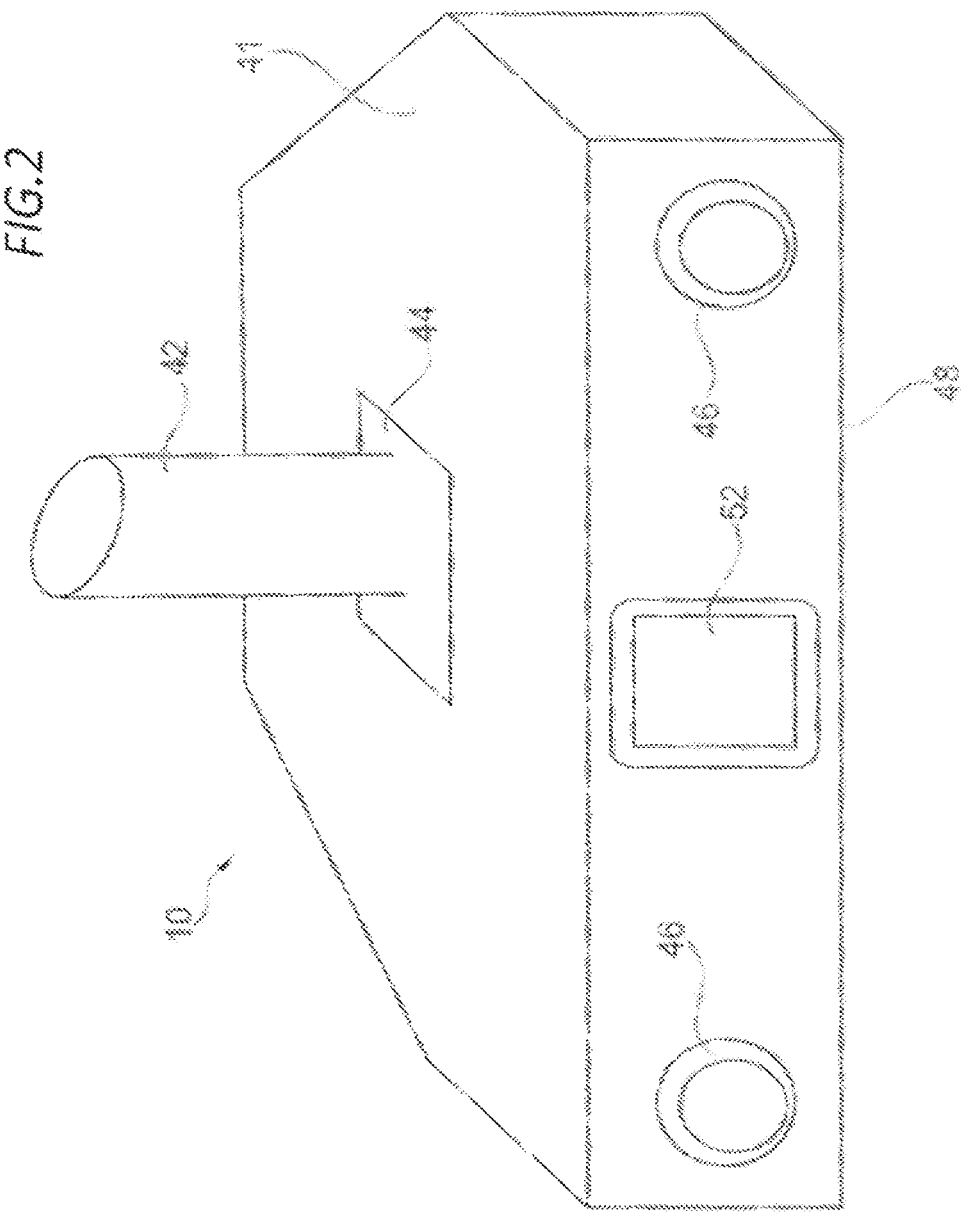
FIG. 2 is a front perspective view of a camera pod of the patient monitor of FIG. 1.

In this example, a speckle projector 52 is provided in the middle of the front surface 48 of the housing 41 between the two lenses 46 in the camera pod 10 shown in FIG. 2. The speckle projector 52 in this example is arranged to illuminate a patient 20 with a non-repeating speckled pattern of red light so that when images of a patient 20 are captured by the two image detectors mounted within a camera pod 10 corresponding portions of captured images can be more easily distinguished. To that end the speckle projector comprises a light source such as a LED and a film with a random speckle pattern printed on the film. In use light from the light source is projected via the film and as a result a pattern consisting of light and dark areas is projected onto the surface of a patient 20. In some monitoring systems, the speckle projector 52 could be replaced with a projector arranged to project structured light (e.g. laser light) in the form of a line or a grid pattern onto the surface of a patient 20. In some monitoring systems, the projector 52 could be omitted.

Figure 3:
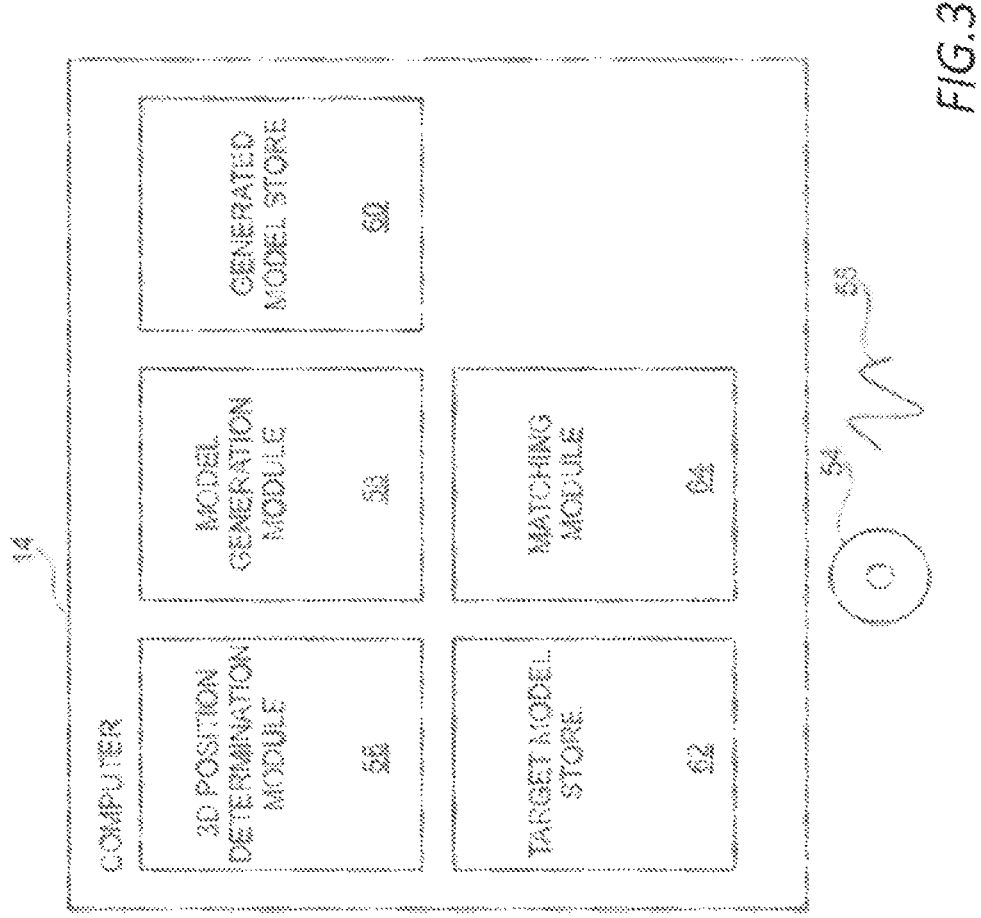
FIG. 3 is a schematic block diagram of the computer system of the patient monitor of FIG. 1.

FIG. 3 is a schematic block diagram of the computer 14 of the patient monitor of FIG. 1. In order for the computer 14 to process images received from the camera pods 10, the computer 14 is configured by software either provided on a disk 54 or by receiving an electrical signal 55 via a communications network into a number of functional modules 56-64. In this example, the functional modules 56-64 comprise: a 3D position determination module 56 for processing images received from the stereoscopic camera system 10, a model generation module 58 for processing data generated by the 3D position determination module 56 and converting the data into a 3D wire mesh model of an imaged surface; a generated model store 60 for storing a 3D wire mesh model of an imaged surface; a target model store 62 for storing a previously generated 3D wire mesh model; and a matching module 64 for determining rotations and translations required to match a generated model with a target model.

In use, as images are obtained by the image capture devices/cameras of the camera pods 10, these images are processed by the 3D position determination module 56. This processing enables the 3D position determination module to identify 3D positions of corresponding points in pairs of images on the surface of a patient 20. In the exemplary system, this is achieved by the 3D position determination module 56 identifying corresponding points in pairs of images obtained by the camera pods 10 and then determining 3D positions for those points based on the relative positions of corresponding points in obtained pairs of images and stored camera parameters for each of the image capture devices/cameras of the camera pods 10.

The position data generated by the 3D position determination module 56 is then passed to the model generation module 58 which processes the position data to generate a 3D wire mesh model of the surface of a patient 20 imaged by the stereoscopic cameras 10. The 3D model comprises a triangulated wire mesh model where the vertices of the model correspond to the 3D positions determined by the 3D position determination module 56. When such a model has been determined it is stored in the generated model store 60.

When a wire mesh model of the surface of a patient 20 has been stored, the matching module 64 is then invoked to determine a matching translation and rotation between the generated model based on the current images being obtained by the stereoscopic cameras 10 and a previously generated model surface of the patient stored in the target model store 62. The determined translation and rotation can then be sent as instructions to the mechanical couch 18 to cause the couch to position the patient 20 in the same position relative to the treatment apparatus 16 as the patient 20 was were when the patient 20 was previously treated.

Subsequently, the image capture devices/cameras of the camera pods 10 can continue to monitor the patient 20 and any variation in position can be identified by generating further model surfaces and comparing those generated surfaces with the target model stored in the target model store 62. If it is determined that a patient 20 has moved out of position, the treatment apparatus 16 can be hafted or a warning can be triggered and the patient 20 repositioned, thereby avoiding irradiating the wrong parts of the patient 20.

A conventional approach to identifying the relative location of the cameras of a monitoring system relative to the isocenter of a treatment room will now be described with reference to FIGS. 4 and 5.

Figure 4:
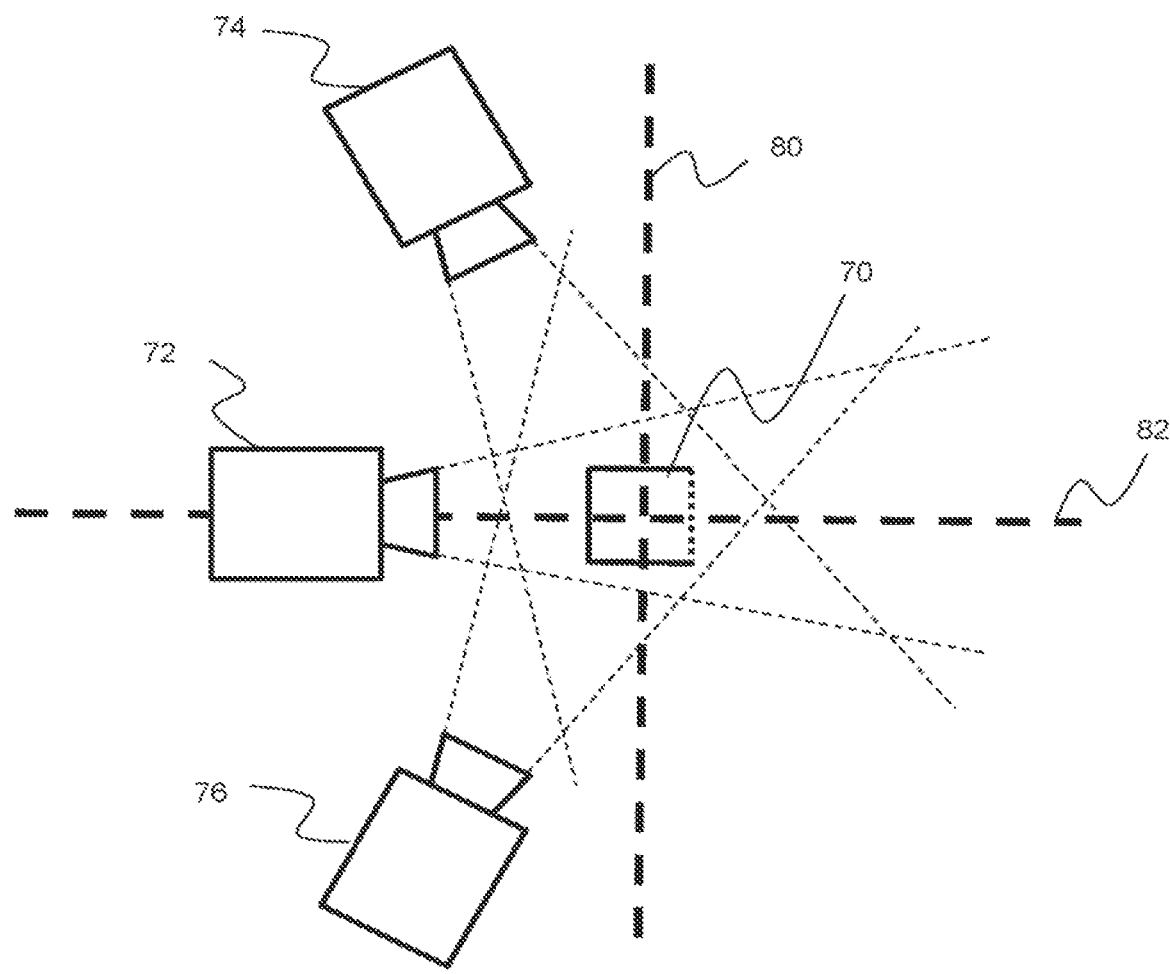
FIG. 4 is a plan view of a conventional arrangement of a calibration cube for identifying the relative location of a camera system and the isocenter of a treatment room.
Figure 5:
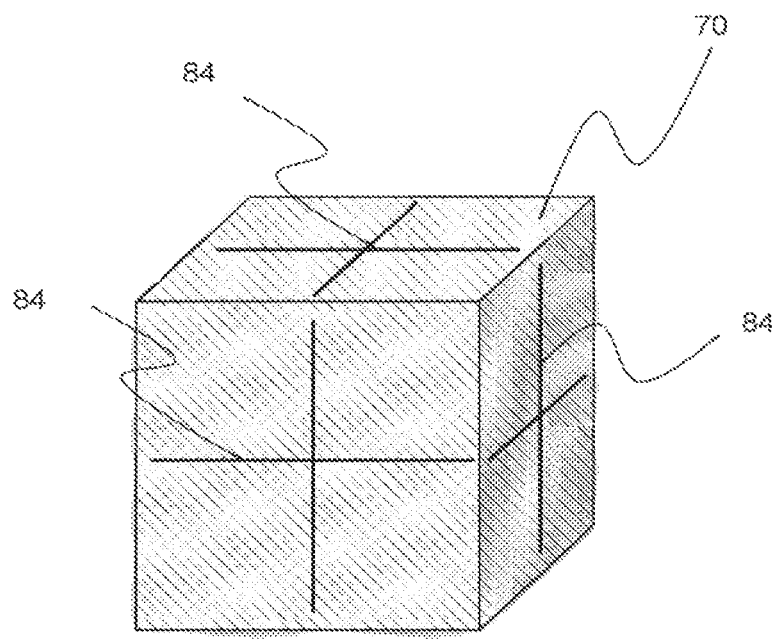
FIG. 5 is a schematic perspective view of a conventional calibration cube for identifying the relative location of a camera system and the isocenter of a treatment room.

FIG. 4 is a schematic plan view of calibration phantom which in this example is in the form of a calibration cube 70 being imaged by three cameras or camera pods 72-76. When identifying the relative location of the cameras of a monitoring system relative to the isocenter of a treatment room, the calibration cube 70 is located with the center of the calibration cube 70 at the isocenter of the treatment room. This is achieved by identifying the location of the isocenter using conventional techniques and highlighting the location of the isocenter by the intersection of three planes of laser light, two of which 80, 82 are shown by the heavy dashed lines in FIG. 4. The third plane (not illustrated in FIG. 4) would be orientated parallel with the surface of the Figure identifying the "height" of the isocenter relative to the surface of the Figure.

As is shown in the Figure, typically the camera pods 72-76 are located a distance away from the location of the isocenter so as not to interfere with the movement of the treatment apparatus 16 as it irradiates the isocenter from different angles and positions. Typically in a patient monitoring system three camera pods 72-76 are provided and, as shown in FIG. 4, are arranged with a central camera pod 72 flanked by two other camera pods 74,76. These secondary camera pods 74,76 are often located as is shown in FIG. 4 symmetrically either side of the central camera pod 72 and on the same side of the treatment room isocenter as the central camera pod 72. In some systems, secondary camera pods 74,76 may be arranged so to be located on either side of the isocenter and substantially in line with the isocenter (i.e. with a line of sight substantially orientated along the line of plane of laser light 80 highlighting the isocenter of the treatment room).

When identifying the relative location of the cameras of a monitoring system relative to the isocenter of a treatment room, the calibration cube 70 is orientated so that in planview one of the surfaces of the calibration cube 70 is substantially parallel with the image plane of the cameras/image detectors of the central camera pod 72. Typically this orientation is achieved by aligning the image plane of the central camera pod 72 in plan-view so as to be parallel with one of the planes 80 of light highlighting the position of the treatment room isocenter. Markings are then provided on the surfaces of the cube enabling the calibration cube 70 to be correctly aligned so that the surface of the cube facing the central camera pod 72 is parallel with the image planes of the cameras/image detectors of the central pod 72 and positioned with the center of the calibration cube 70 at the treatment room isocenter 70. Typically such markings are in the form of a cross 84 on each of the surfaces of the calibration cube, as is illustrated in FIG. 5.

When generating a model from images of a calibration cube 70, the accuracy with which a model can be generated typically decreases for surfaces imaged at an oblique angle and for that reason surfaces of a calibration cube 70 are typically preferentially modelled using image data which views a surface at the least oblique angle.

Orientating the cube, with a front surface of the calibration cube 70 substantially parallel with the image plane of cameras/image detectors of a central camera pod 72, minimizes the angle at which the central camera pod 72 views the calibration cube 70 and, in an orientation such as is illustrated in FIG. 4, the other camera pods 74,76 view the surfaces of the calibration cube 70 closest to them at a slight angle.

With the calibration cube 70 located with the center of the cube located at the treatment room isocenter and with the surface of the cube 70 parallel with the image plane of the cameras/image detectors of the central camera pod 72, the planes of laser light highlighting the isocenter of the treatment room should coincide with the markings 84 on the calibration cube 70.

When the calibration cube 70 has been located with the center of the cube located at the treatment room isocenter, the cameras/image detectors of the camera pods 72-76 capture images of the calibration cube 70. These images are then passed to the computer 14 which processes the images to identify the 3D locations of points on the surface of the calibration cube 70. The relative location of the treatment room isocenter in the model space of the monitoring system can then be identified as the center of a best fit for a model of the calibration cube 70 to the identified points of the surface of the cube based on the processed images.

The applicants have appreciated that where, as is typical in a patient monitoring system, multiple camera pods are located on the same side of a treatment room isocenter, when imaging a calibration cube 70, typically none of the cameras obtain images of the surface of the calibration cube 70 which lies on the other side of the isocenter.

Thus for example in the case of the monitoring system illustrated in FIG. 4, where the view points of the camera pods 72-76 are illustrated by dotted lines extending away from the schematic illustrations of the camera pods 72-76, none of the camera pods 72-76 obtain images of the surface of the calibration cube 70 remote from the central camera pod 72, highlighted in FIG. 4 as the surface of the calibration cube 70 on the right hand side of the cube 70 and highlighted as a dotted line.

The applicants have further appreciated that this failure to obtain images of that surface of the calibration cube 70 is a potential source of error in determining the location of the treatment room isocenter in the model space of the monitoring system.

Figure 6:
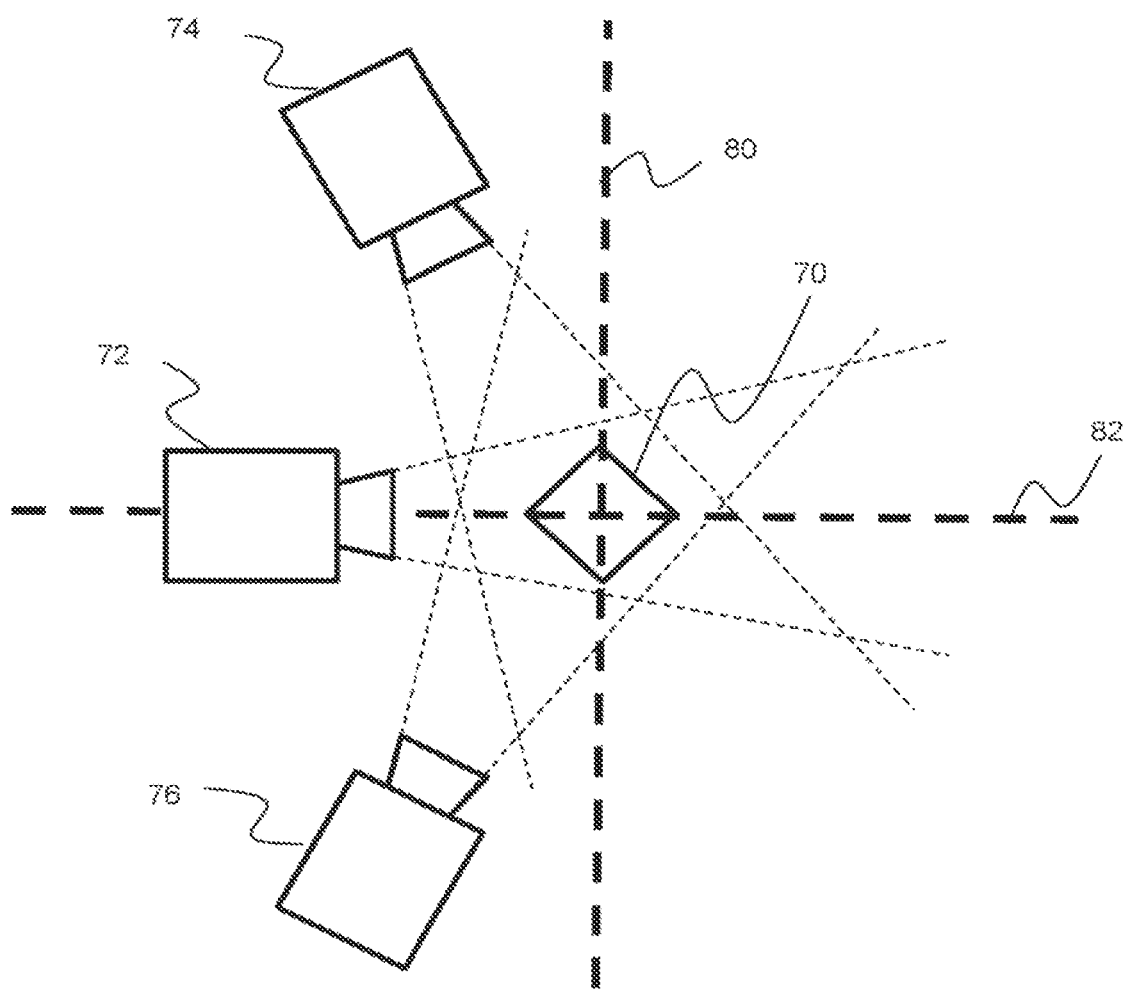
FIG. 6 is a plan view of an arrangement of a calibration cube for identifying the relative location of a camera system and the isocenter of a treatment room in accordance with an embodiment of the present invention.

To address this issue, the applicants propose that rather than positioning a calibration cube 70 in the manner illustrated in FIG. 4 where the surface of the calibration cube 70 is aligned to be substantially parallel with the image plane of the cameras/detectors of a central camera pod 72, the calibration should instead be orientated as illustrated in FIG. 6 (i.e. rotated by 45° so that in plan-view the surfaces of the calibration cube 70 closest to the central camera pod 72 are at 450 relative to the image plane of the central camera pod 72 with one edge of the cube being pointed towards the camera pod 70). As shown in FIG. 6, in such an orientation the surfaces of the calibration cube 70 remote from the central camera are imaged by the other camera pods 74, 76.

In the orientation shown in FIG. 6, it will be appreciated that the surfaces of the calibration cube 70 imaged by the central camera pod 72 are at a more oblique angle to the image plane of the cameras/image detectors of the camera pod 72, than when the calibration cube 70 is orientated as in FIG. 4. Although this is the case, where the relative angle of orientation is around 45°, the applicants have found that this does not make any significant reduction in the accuracy with which the 3D position of the surfaces can be modelled.

It will also be appreciated that as illustrated, the surfaces of the calibration cube remote from the central camera pod 72 are only imaged by the other camera pods 74,76 at a relatively oblique angle. Ordinarily modelling the 3D positions of surfaces imaged at a relatively oblique angle is relatively inaccurate. However, although this is the case, the applicants have determined that any inaccuracies are more than compensated for by the ability of a monitoring system to image and hence model a greater proportion of the surface area of the calibration cube 70.

Although not fully apparent in the plan view images of FIGS. 4 and 6, it should be borne in mind that typically as is shown in FIG. 1 camera pods of a patient monitoring system are suspended from the ceiling of a treatment room and are located above the plane of the treatment room isocenter. Thus in the case of the orientation of a calibration cube 70 as shown in FIG. 4, a portion of the upper surface of the calibration cube remote from the camera pods 72-76 is viewed at a more oblique angle than portions of the surface closer to the camera pods 72-76. This limits the ability of the system to generate an accurate model of the portions of the cube viewed at a more oblique angel and in the case of the orientation illustrated in FIG. 4, typically only the portion of the calibration cube 70 closest to the camera pods 72-76 is modelled.

Compared with the orientation illustrated in FIG. 4, additional information is obtained when a calibration cube 70 orientated as shown in FIG. 6 is imaged, as even if only a small portion of the calibration cube 70 located on the far side of the plane indicated by the plane of laser light 80 can be modelled, the fact that three corners of the upper surface can be identified, together with pre-knowledge of the dimensions of the calibration cube 70, allows more accurate identification of the location of the calibration cube 70. Whereas in contrast, when orientated as shown in FIG. 4, modelling the portion of the calibration cube 70 closest to the camera pods 72-76 only results in the modelling of two of the corners of the cube.

The applicants have determined that, contrary to expectation, the additional information about the corners of the cube, as orientated in FIG. 6, is of greater importance in identifying the location of a treatment room isocenter, than inaccuracies which arise due to the camera pods 72-76 imaging the front portion of a calibration cube 70 at a more oblique angle or imaging the remote portions of a calibration cube 70 only at a relatively oblique angle and hence positioning a calibration cube with surfaces in plan-view at c. 45° to the image plane of a central camera pod 72 improves the accuracy with which the a treatment room isocenter can be identified in the model space of a monitoring system.

Orientating a calibration cube 70 in the manner illustrated in FIG. 6, facilitates the modelling of the corner of the calibration cube 70 closest to the central camera pod 72 using image data from all three camera pods 72-76 both individually and collectively without reliance upon image data obtained at a highly oblique angle. This together with knowledge of the dimensions of the calibration cube 70 should enable the location of the center of the cube in camera space to be identified.

If all three camera pods are perfectly calibrated models of the surfaces generated by identifying matching portions of images from each individual camera pod should all be aligned. However, inevitably minor errors do arise. In the configuration illustrated, the camera pods 72-76 are arranged symmetrically. To the extent that errors arise when modelling the surface of the calibration cube 70 using the outer two camera pods 74,76 such errors should cancel each other out with the model surface generated by the central camera pod 72 identifying a surface close to the average of the surfaces generated using images from the other camera pods 74,76 and hence collectively the three camera pods should enable the position of the corner of the calibration cube 70 closest to the central camera pod 72 to be accurately identified with limited error.

Figure 7:
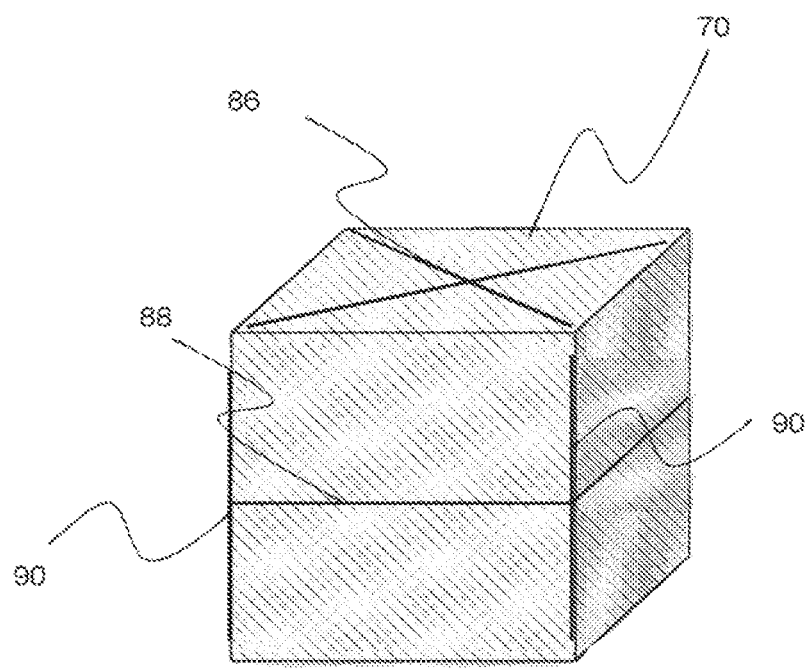
FIG. 7 is a schematic perspective view of a calibration cube for identifying the relative location of a camera system and the isocenter of a treatment room in accordance with an embodiment of the present invention.

The positioning of a calibration cube 70 in the manner illustrated in FIG. 6, with the surface of the cube in plan-view angled at 45° relative to the camera plane of a central camera pod 72 orientated in line with the treatment room isocenter, can be facilitated by providing a calibration cube 70 marked as indicated in FIG. 7. In contrast to the convention markings on a calibration cube 70 as illustrated in FIG. 5, in FIG. 7 the conventional cross markings 84 shown in FIG. 5 are replaced by a diagonal cross 86 extending between opposite corners of the cube 70 on the upper surface of the cube, a line 88 bisecting the calibration cube 70 and a series of lines 90 highlighting the edges of the cube 70.

When arranging the calibration cube 70 in the manner indicated in FIG. 6, the modified markings 86-90 facilitate the arrangement of the calibration cube 70 as the cube can be located with its center at the treatment room isocenter by aligning the planes of the laser light 80,82 used to identify the treatment room isocenter with the modified markings 86-90 on the calibration cube 70.

Although in the above, a method of identifying the locations of cameras in a monitoring system relative to a treatment room isocenter has been described in the context of a monitoring system utilizing a stereoscopic camera system, it will be appreciated that the above described method where the front surface of a calibration cube in plan-view is imaged at an angle of approximately 45° relative to the image plane of a camera/image detector of a central camera pod is equally applicable to the calibration of other types of camera based patient monitoring system. Thus for example rather than identifying the locations of cameras in a stereoscopic camera based monitoring system, the above described approach could equally be applied to determining the relative locations of cameras and a treatment room isocenter in a time of flight based monitoring system or alternatively a monitoring system based upon imaging the projection of structured light onto a surface being monitored.

Although in the above, the calibration of a monitoring system has been described wherein a calibration cube 70 is positioned at a treatment room isocenter highlighted by the intersection of three planes of laser light, it will be appreciated that the above described method could equally be applied to other methods of identifying the relative locations of a cameras in a patient monitoring system and the isocenter.

Thus for example, rather than relying upon the identification of the treatment room isocenter being identified by the intersection of a planes of laser light an approach such as the approach described in Vision RT's earlier US Patent Application, US 2016-129283 could be utilized.

In such an approach, initially a calibration phantom in the form of a calibration cube containing irradiation targets, such as one or more small metallic balls or other metal targets made of steel, titanium or tungsten or the like, is positioned with the phantom's center at an estimated location for the isocenter of a radio therapy treatment apparatus with the front surface of the calibration cube in plan-view angled at approximately 45° relative to the image plane of a camera forming part of a monitoring system. The calibration phantom is then irradiated using the radio therapy treatment apparatus. The relative location of the center of the calibration phantom and the isocenter of the radio therapy treatment is then determined by analyzing radiographic images of the irradiation of the calibration phantom containing the irradiation targets.

In some embodiments, the calibration phantom can then be repositioned by, for example, sending instructions to a moveable couch on which the calibration phantom is mounted so as to apply an offset corresponding to the determined relative location of the center of the calibration phantom and the isocenter of the radio therapy treatment apparatus to the calibration phantom. The relative location of the cameras of the monitoring system and the treatment room isocenter can then be determined by capturing images of the repositioned calibration cube positioned so as have its center located at the treatment room isocenter.

Alternatively, as is proposed in US 2016-129283, the relative locations of the cameras and the treatment room isocenter could be determined without physically relocating the calibration cube. More specifically, the calibration cube could be positioned in the manner described above at an estimated location for the isocenter of a radio therapy treatment apparatus. Images of the calibration cube with the front surface of the calibration cube in plan-view angled at approximately 45° relative to the image plane of a camera forming part of a monitoring system could then be obtained and a 3D computer model of the surface of the cube could then be generated. The calibration cube could also be irradiated without the cube being repositioned and radiographic images of the irradiated cube and in particular irradiation targets within the cube could be obtained and processed to determine the relative location of the cube and the treatment room isocenter. The location of the treatment room isocenter relative to the positions of the cameras of the monitoring system could then be determined based on any offset determined by analyzing the radiographic images and the representation of the cube in camera space generated by processing images captured by the monitoring apparatus.

It will be appreciated that adopting either approach described above avoids errors arising due to any inaccuracies with which the laser highlighting system identifies a treatment room isocenter as in either approach the treatment room isocenter is determined through the analysis of the images of the irradiation of targets contained within the calibration cube 70. In such embodiments, it would be possible to omit the presence of a laser highlighting system. However, preferably the laser highlighting system would not be omitted as a laser highlighting system, together with markings 86-90 on the surface of a calibration cube 70 facilitates an initial positioning of a calibration cube in the correct orientation and with its center very close to, if not perfectly aligned with, a treatment room isocenter.

Although, in the example illustrated in FIGS. 4 and 6, a group of camera pods 72-76 are shown where all of the camera pods are located on the same side of a plane passing through the isocenter of the treatment room, it will also be understood that the camera pods 72-76 might be arranged in a different configuration.

Figure 8:
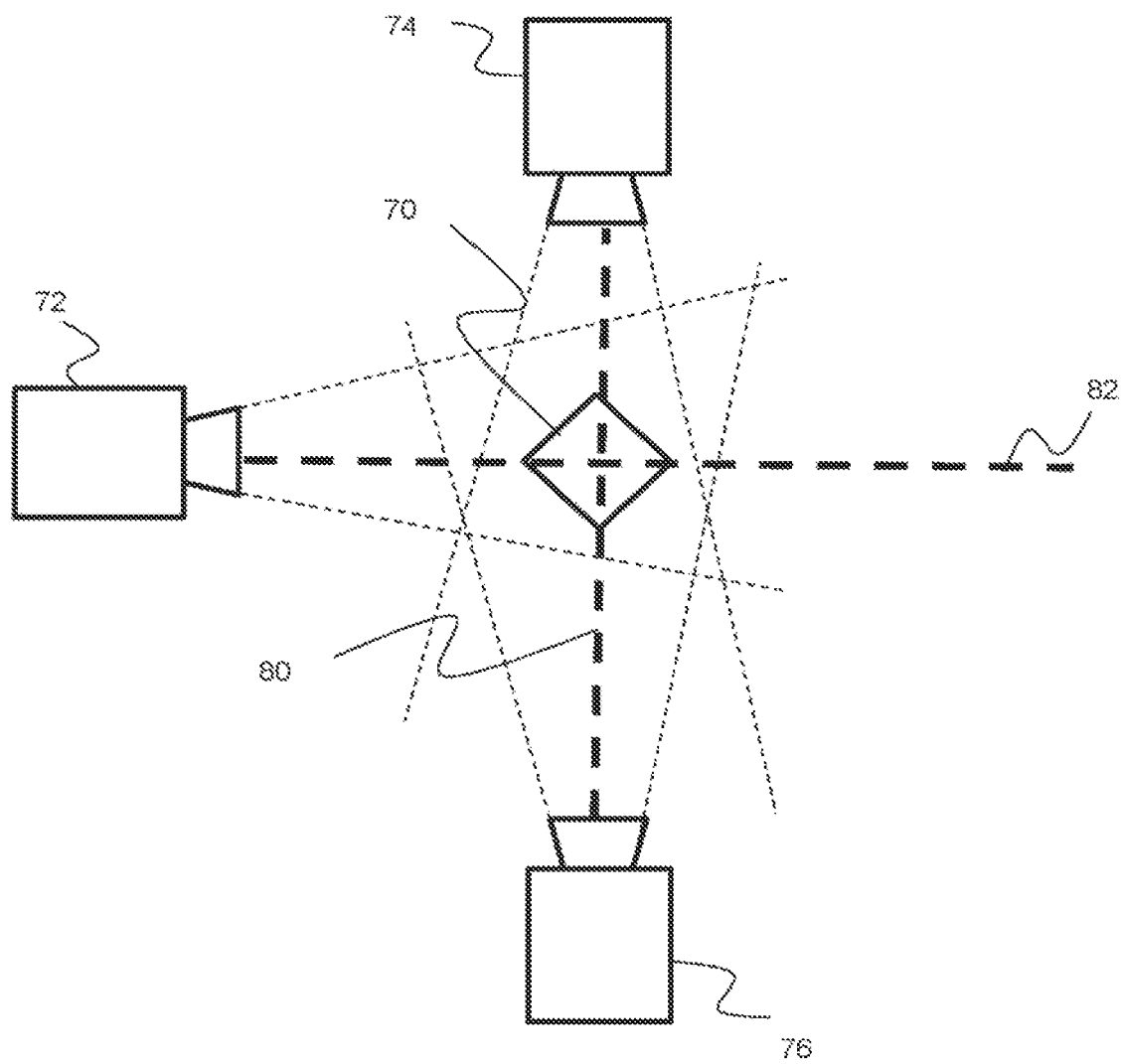
FIGS. 8-10 are plan views of arrangements of a calibration cube for identifying the relative location of a camera system and the isocenter of a treatment room in accordance with further embodiments of the present invention.

In particular it will be appreciated that the above described approach to calibration of a monitoring system would equally apply to a monitoring system where the secondary camera pods 74,76 are aligned with a plane passing through the treatment room isocenter parallel or substantially parallel to the image plane of the cameras/image capture devices of a central camera pod 72 such as is illustrated in FIG. 8. In such a configuration, as is shown in FIG. 8, each of the surfaces closest to each of the cameras 72-76 is at approximately 45° in plan-view angled relative to the image plane of the camera imaging that surface. Thus in such a configuration, the relative obliqueness at which the camera's view the calibration phantom 70 is minimized while still enabling the monitoring system to view all four sides and the top surface of the calibration phantom 70. In the case of the calibration of a camera system comprising three camera pods 72-76 where two of the camera pods 74,76 are arranged substantially symmetrically either side of a central camera pod 72, angling the surface of the cube in plan-view so as to be at approximately 45° relative to the image plane of the cameras/image capture devices of a central camera pod 72 is preferable because the symmetry of the arrangement of the camera pods 74,76 and the symmetry of the calibration cube 70 causes the secondary camera pods 74,76 to capture similar images of the calibration cube 70 and hence any errors arising based on the images captured by the secondary camera pods 74,76 when determining the location of the calibration cube should cancel each other out.

Figure 9:
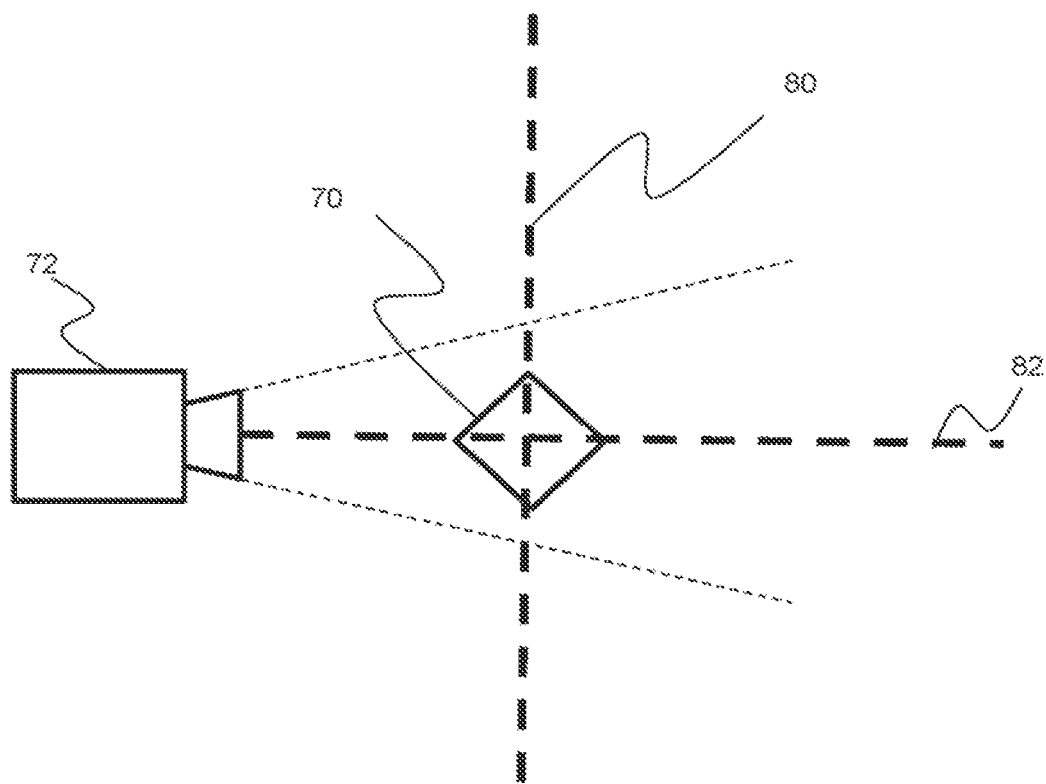

It will also be appreciated that in other embodiments a monitoring system involving a single camera pod (e.g. the central camera pod 72 alone) could be calibrated utilizing the approach described above orientating a calibration cube 70 so that the front surface of the cube (i.e. the surface closest to the image plane of the camera/image detectors with the camera pod 72 monitoring the cube in plan-view was inclined relative to the image plane of the camera(s)) such as is illustrated in FIG. 9.

Figure 10:
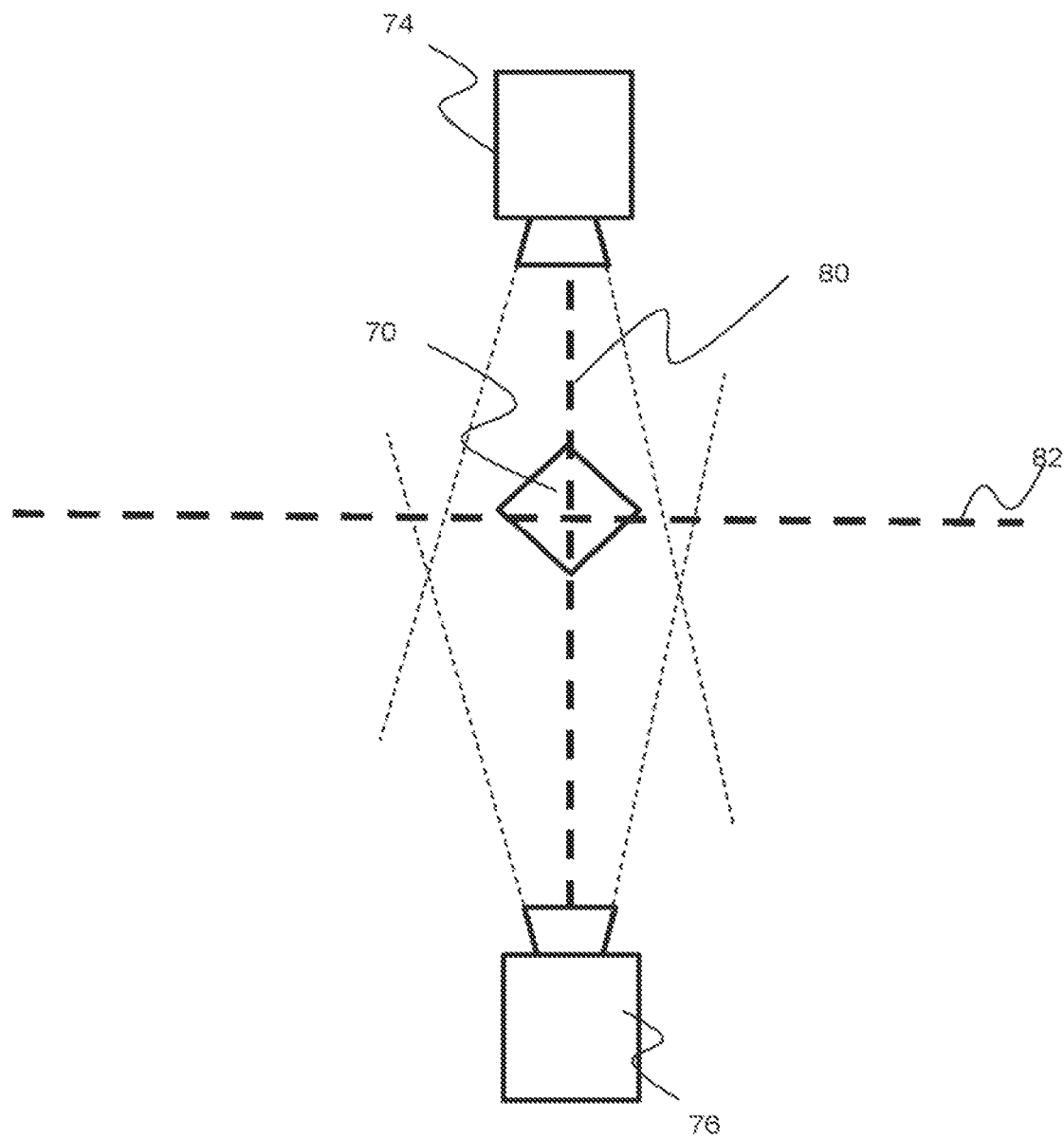

It will also be appreciated that in other systems, the central camera pod 72 might be omitted and instead a monitoring system including pair of camera pods 74,76 might be calibrated using the approach described above such as is illustrated in FIG. 10.

Although in the above described embodiments the alignment of the calibration cube has been described as being such that the surfaces of the cube in plan-view are at approximately 45° relative to the image plane of the cameras/image capture devices of a camera pod 72, it will be appreciated that the alignment of the cube need not be exactly at 45° in order to obtain the benefits of the current invention and that some deviation from 45° would be permissible.

The invention claimed is:

1. A method of determining the relative location of an image capture device of a monitoring system for monitoring the positioning of a patient during radiation treatment and an isocenter of a treatment room towards which a treatment apparatus is arranged to direct radiation, the method comprising:
   locating a calibration phantom in a treatment room, wherein in plan-view at least one surface of the calibration phantom closest to at least one image capture device is inclined approximately 45° relative to the camera plane of that image capture device;
   obtaining an image of the calibration phantom using the image capture device;
   processing the obtained image to identify the relative location of the calibration phantom and the camera plane of the image capture device; and
   utilizing the identified location of the calibration phantom and the camera plane of the image capture device to determine the relative location of the camera plane of the image capture device and the isocenter of a treatment room towards which the treatment apparatus is arranged to direct radiation.

2. A method in accordance with claim 1 wherein
   the calibration phantom is configured to be located approximately at the isocenter of the treatment room using a lighting system to highlight the isocenter of the treatment room; and,
   wherein locating the calibration phantom by aligning light from the lighting system with markings provided on the exterior of the calibration phantom.

3. A method in accordance with claim 2 wherein the calibration phantom comprises a cube having markings provided on the exterior; which markings are selected from a group comprising markings extending along the edges of the cube; markings bisecting the cube; and a cross extending between diagonally opposite corners of the cube.

4. A method in accordance with claim 1 wherein the calibration phantom contains one or more irradiation targets, the method further comprising:
   obtaining a radiographic image of the calibration phantom irradiated by the treatment apparatus;
   analyzing the obtained radiographic image of the calibration phantom to determine the relative location of the treatment room isocenter and the calibration phantom.

5. A method in accordance with claim 4, further comprising repositioning the calibration phantom so that the calibration phantom is located at the isocenter of the treatment room.

6. A method in accordance with claim 1 wherein the monitoring system comprises a plurality of image capture devices for providing stereoscopic images of the calibration phantom.

7. A method in accordance with claim 6 wherein the monitoring system further comprises a projector operable to project light onto the surface of an object located in the vicinity of the isocenter of the treatment room.

8. A method in accordance with claim 7 wherein the projector is operable to project structured light in the form of a grid pattern or a line of laser light onto the at least one surface of the calibration phantom located in the vicinity of the isocenter of the treatment room, wherein the processing an obtained image comprises generating a model, of the imaged at least one surface of the calibration phantom onto which structured light has been projected, on the basis of the distortion of a pattern of structured light appearing in the image.

9. A method in accordance with claim 7 wherein the projector is operable to project a speckled pattern of light onto the at least one surface of the calibration phantom located in the vicinity of the isocenter of the treatment room, wherein the processing an obtained image comprises generating a model, of the imaged at least one surface of the calibration phantom onto which a speckled pattern of light has been projected, on the basis of identification of corresponding portions of the at least one imaged object in stereoscopic images.

10. A method in accordance with claim 1 wherein the monitoring system comprises one or more camera pods each containing one or more image capture devices wherein the locating a calibration phantom approximately at the isocenter of the treatment room, wherein the at least one surface of the calibration phantom closest to one of the camera pods is inclined approximately 45° relative to the camera plane of the image capture device on that camera pod.

11. A method in accordance with claim 10 wherein the one or more camera pods comprise a plurality of image capture devices and the camera pods are all located on the same side of a treatment room.

12. A method in accordance with claim 11 wherein the locating a calibration phantom approximately at the isocenter of a treatment room, wherein in plan-view the of the at least one surface of the calibration phantom closest to an image capture device of a centrally located camera pod, flanked by two other camera pods is inclined approximately 45° relative to the camera plane of the image capture device on the centrally located camera pod.

13. A method in accordance with claim 10 wherein the one or more camera pods are arranged in a symmetrical pattern within the treatment room.

14. A method in accordance with claim 10 wherein the camera pods are suspended from the ceiling of the treatment room.

15. A monitoring system for monitoring the positioning of a patient during radiation treatment and comprising:

at least one image capture device configured to obtain an image of at least one surface of a calibration phantom wherein in plan-view the at least one surface closest to the image capture device is inclined approximately 45° relative to camera plane of the image capture device; and a computer configured to receiving the obtained image from the image capture device, to determining the relative location of the calibration phantom and the camera plane of the image capture device, and to utilizing the identified location of the calibration phantom and the camera plane of the image capture device to determine the relative location of the camera plane of the image capture device and the isocenter of the treatment room towards which the treatment apparatus is arranged to direct radiation.

16. A monitoring system in accordance with claim 15 further comprising a lighting system to highlight the isocenter of a treatment room and wherein the lighting system is configured to aligning light to highlight the isocenter of a treatment room with markings provided on the exterior of the calibration phantom.

17. A monitoring system in accordance with claim 15 wherein the calibration phantom contains one or more irradiation targets.

18. A monitoring system in accordance with claim 15 further comprising a projector configured to project light onto the surface of an object located in the vicinity of the treatment room isocenter.

19. A monitoring system in accordance with claim 15, wherein the at least one image capture device comprises a plurality of image capture devices configured for providing stereoscopic images of the calibration phantom.

* * * * *